United States Patent [19]

DuBois et al.

[11] 4,226,804

[45] Oct. 7, 1980

[54] ALPHA AMINO ACID DIHYDROCHALCONES

[75] Inventors: Grant E. DuBois, Palo Alto; Rebecca A. G. Stephenson, Redwood City; Guy A. Crosby, Palo Alto, all of Calif.

[73] Assignee: Dynapol, Palo Alto, Calif.

[21] Appl. No.: 19,054

[22] Filed: Mar. 9, 1979

[51] Int. Cl.$^2$ ............... C07C 101/72; A23L 1/236
[52] U.S. Cl. ............... 260/501.11; 260/345.2; 260/429.9; 260/448 R; 426/548; 562/444
[58] Field of Search ............... 562/444; 260/501.11, 260/429.9, 448 R

[56] References Cited

U.S. PATENT DOCUMENTS

| | | | |
|---|---|---|---|
| 3,087,821 | 4/1963 | Horowitz et al. | 426/548 |
| 3,322,775 | 5/1967 | Cragoe, Jr. | 562/444 |
| 3,855,301 | 12/1974 | Rizzi | 260/590 |
| 3,956,375 | 5/1976 | Farkas et al. | 562/464 |
| 3,974,299 | 8/1976 | Dubois et al. | 426/548 |
| 3,976,790 | 8/1976 | Crosby et al. | 426/3 |
| 4,055,678 | 10/1977 | Crosby et al. | 260/511 |

FOREIGN PATENT DOCUMENTS

2148332 4/1972 Fed. Rep. of Germany.

*Primary Examiner*—G. T. Breitenstein
*Attorney, Agent, or Firm*—William H. Benz

[57] ABSTRACT

Dihydrochalcones of the formula

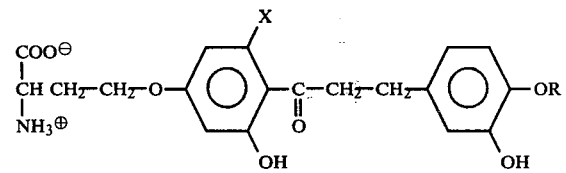

are disclosed wherein X is H or OH and R is lower alkyl. These materials are useful as sweeteners for edibles. A process for preparing these compounds using a novel intermediate is disclosed as are acid and base neutralization products of the subject dihydrochalcones.

13 Claims, No Drawings

ALPHA AMINO ACID DIHYDROCHALCONES

BACKGROUND OF THE INVENTION

1. Field of the Invention

This invention concerns synthetic sweeteners. More particularly, it concerns a new group of dihydrochalcone compounds and their use as sweeteners for edible compositions such as foodstuffs.

2. Discussion of the Prior Art

Dihydrochalcones are compounds having a

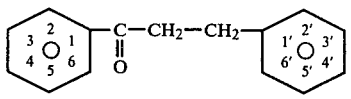

basic structure. Various examples of dihydrochalcones have been known since the 1930s. The members of this class of dihydrochalcones vary from one another by the nature and placement of substituents on the aromatic rings.

In 1963 it was discovered that some, but by no means all, of the dihydrochalcones are sweet (Horowitz and Gentili, U.S. Pat. No. 3,087,821, issued Apr. 30, 1963). The earliest examples of sweet dihydrochalcones were derived from naturally occurring flavanones having bulky saccharide residues attached at position 4. More recently, several sweet dihydrochalcones having smaller and simpler substituents at their 4 position have been disclosed. Such disclosures include Rizzi, U.S. Pat. No. 3,855,301, issued Dec. 17, 1974; Rizzi, U.S. Pat. No. 3,751,270, issued Aug. 7, 1973; Farkus et al., U.S. Pat. No. 3,956,375, issued May 11, 1976; Crosby et al., U.S. Pat. No. 3,974,299, issued Aug. 10, 1976; Crosby et al., U.S. Pat. No. 3,976,790, issued Aug. 24, 1976; Crosby et al., U.S. Pat. No. 4,055,678, issued Oct. 25, 1977 and U.S. Ser. No. 964,211, filed by Crosby et al. on Dec. 1, 1978.

Among the prior art references, the last mentioned patents and application of Crosby et al. disclose compounds which are considered to be structurally closest to the present materials. The prior art compounds have substituents in the 2, 6 and 4' positions which are the same as those of the present compounds. Importantly, however, these references do not show or suggest the alpha amino acid 4 position substituent which the present compositions require. All employ groups which are chemically far different from the present alpha amino acid.

If there is one fact that may be derived from the prior art, it is that no underlying taste-structure relationship has been developed or proved for the dihydrochalcones. Changes which are chemically minor on their face may have a major effect on taste properties. The taste/structure relationship still is largely empirical and not predictable.

STATEMENT OF THE INVENTION

The present invention is a new class of sweet dihydrochalcones. These materials are classifiable as 4-(3-amino-3-carboxypropoxy)-dihydrochalcones. They are represented structurally in their most common ionic state as shown in General Formula I.

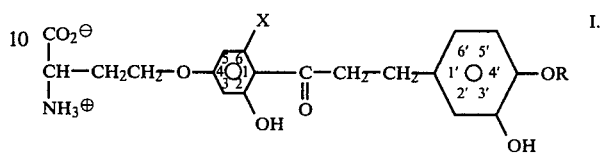

wherein R is a lower saturated alkyl of from 1 to 4 carbons inclusive, and X is hydrogen or hydroxy. These materials may be named 2,3'6-trihydroxy and 2,3'-dihydroxy-4-(3-amino-3-carboxypropoxy)-4'-alkoxydihydrochalcones.

These compounds contain several ionizable protons and a cationic group subject to protonation. This means that at pHs below about 3 or above about 8, additional ionic forms of the dihydrochalcones are present in significant amounts.

At low pHs the carboxyl group protonates to give the compound shown in General Formula II.

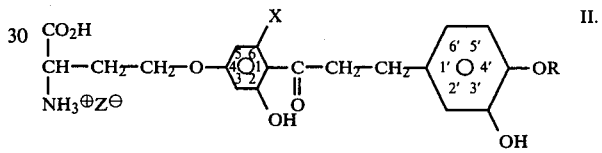

wherein X and R are previously defined and $Z^-$ is a physiologically acceptable conjugate base of a strong acid.

Depending upon the identity of X, the compounds of Formula I have 2 or 3 labile hydrogens which can be ionized at high pHs. One hydrogen can be ionized from the amine at pHs above about 8. At about the same pH a hydrogen can be ionized from the 6 position hydroxyl (i.e., if X is OH). The 3' hydroxyl can give up a hydrogen as well, but this hydrogen is one or two orders of magnitude less acidic than the first two. If X is hydrogen, instead of hydroxyl, obviously, the molecule can give up at most two protons.

The high pH forms of the compound may be depicted structurally as shown in General Formula III.

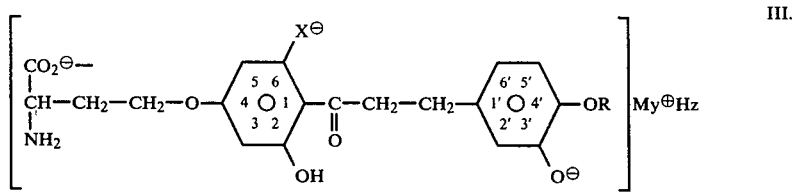

wherein R is as previously defined, $M^+$ is a physiologically acceptable cation; X is hydrogen or oxy, and y and z are each positive numbers, the sum of which totals 2 when X is hydrogen or 3 when X is oxy.

Each of these forms of the compounds of this invention constitutes an aspect of the invention as does the use of these materials to impart sweet flavors to foods, beverages, medicaments and other comestibles.

These compounds may be formed by substituting the 7 position of the flavanones shown in General Formula IV.

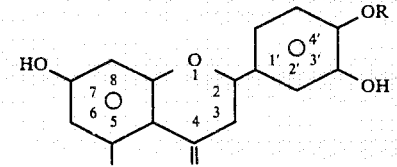

with the electrophilic substitution reagent methyl 2-(N-carbobenzyloxy)amino-4-bromobutyrate or the like and thereafter hydrogenating and opening the flavanone to the dihydrochalcone.

DETAILED DESCRIPTION OF THE INVENTION

The Compounds

The compounds of the present invention in their most common state have the structure shown in General Formula I. In that Formula R is an alkyl, more particularly a 1, 2, 3, or 4 carbon alkyl that preferably is linear, i.e., methyl, ethyl n-propyl or n-butyl. Methyl is the most preferred R.

X is either hydrogen or hydroxy, with hydroxy being preferred. $M^+$ is a physiologically acceptable cation. As used herein, a "physiologically acceptable cation" is defined to include ammonium and the cations of the third and fourth period metals which are nontoxic, especially Na(I), K(I), Mg(II), Ca(II), Al(III) and Zn(II). Preferred cations are the cations of the third and fourth period group I and II metals, i.e., Na(I), K(I), Mg(II), and Ca(II), with K being the most preferred cation. In structural formulae of this specification, the divalent calcium cation will be shown as $\frac{1}{2}$ Ca$^{++}$ to indicate a charge balance with the monovalent carboxy group. In actual practice, of course, the Ca$^{++}$ is associated with two monovalent dihydrochalcone groups. Mixtures of cations may be used as well.

$Z^-$ is a physiologically acceptable conjugate base of a strong acid such as the mineral acids. As used herein, the term "strong acid" refers to an acid which is at least 90% ionized in pH 3 water while a "physiologically acceptable conjugate base" is a base which is nontoxic. Representative physiologically acceptable conjugate bases of strong acids include $Cl^-$, $HSO_4^-$, $SO_4^=$ and $PO_4^\equiv$.

While it will be appreciated that Formulae I, II and III represent the same compound, but in different ionic states, the form shown in Formula I is the most common and thus generally preferred.

Preparation of the Compounds

The compounds of General Formula I are conveniently formed, in a general sense, by substituting the 7 position of the flavanones shown in General Formula IV.

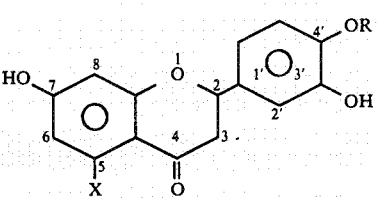

with the electrophilic substitution reagent, methyl 2-(N-carbobenzyloxy)amino-4-bromobutyrate, and thereafter removing protecting groups and converting the flavanone to the desired dihydrochalcone. The flavanones include hesperetin and its X equals hydrogen and R equals $C_2H_5, C_3H_7$ or $C_4H_9$ equivalents. Methyl 2-(N-carbobenzyloxy)amino-4-bromobutyrate has the formula

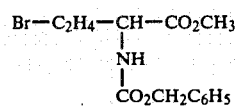

Its preparation and a representative preparation of the subject dihydrochalcones are given in the Examples.

The general preparative scheme for the dihydrochalcones may be shown as follows:

STEP A.

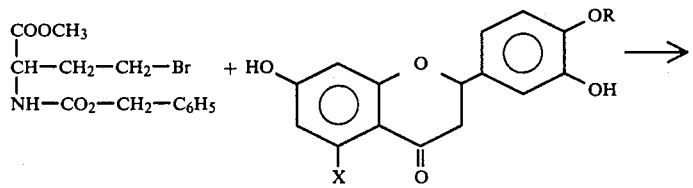

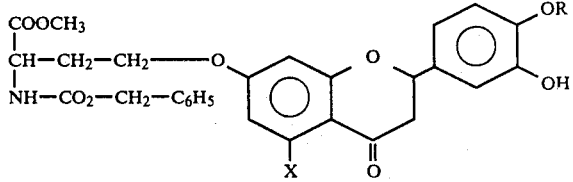

STEP B.

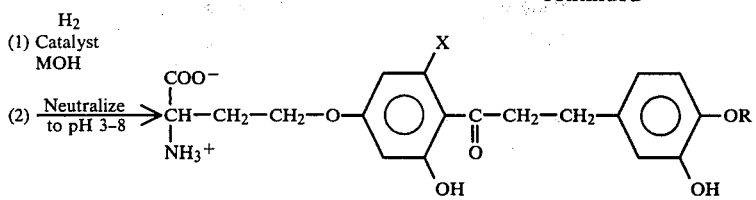

The addition of the bromobutyrate to the flavanone 7 position (Step A, above) is carried out as follows. The bromobutyrate and the flavanone are combined in a liquid phase polar aprotic reaction medium. Suitable media include N,N-dimethylformamide (DMF), dimethylsulfoxide, hexamethylphosphoramide, and the like with DMF generally being preferred. The molar amounts of flavanone and bromobutyrate are about equal with 0.5 to 1.5, preferably 0.6 to 1.4 and most preferably 0.8 to 1.2 equivalents of flavanone per mole of bromobutyrate being employed.

An acid acceptor, such as an alkali metal carbonate, bicarbonate or hydroxide, and preferably $Na_2CO_3$ or $K_2CO_3$, is present during the bromobutyrate substitution reaction. This material is generally present in a molar amount about equal to the moles of flavanone—i.e., 1-1.5 equivalents, basis flavanone. The reaction is carried out under moderate conditions such as temperatures of from 10° C. to 60° C. for times of from 5 to 70 hours. Time, of course, is inversely proportional to temperature. The mixture is generally stirred and blanketed with an inert gas atmosphere. The bromobutyrate substitution product may be recovered and purified by simple art-known techniques such as extraction, crystallization, evaporation of solvent, and the like.

The cleavage and hydrogenation of the flavanones to the dihydrochalcones (Step B, above) is carried out with molecular hydrogen and a suitable catalyst. Mild conditions, such as a gross excess of hydrogen (for example 10 to 100 psi), dilute aqueous base such as 1 to 8 molar, preferably 2 to 6 molar alkali metal hydroxide, particularly KOH or NaOH and a noble metal catalyst such as palladium or platinum, (preferably palladium), preferably supported such as upon charcoal or the like. Times of from a few hours to about 30 hours, with temperatures of from room temperature (20° C.) to say 35° C. may be employed. As earlier noted, more strenuous conditions may be employed, if desired. These conditions also serve to remove the protecting groups on the amine and carboxyl groups.

Following flavanone ring cleavage, hydrogenation, and protecting group removal, the product is recovered, such as by filtration to remove catalyst, evaporation to dryness and chromatography, such as by liquid chromatography or other equivalent chromatographic techniques, or by crystallization, especially in pH range of from 4 to 7. Crystallization is the preferred recovery technique.

The flavanones employed as starting materials in this synthesis include hesperetin and its X and R substituted equivalents. Hesperetin (X=OH, R=CH₃) is available commercially. The other flavanones are less common and generally must be prepared. One preparative route for these flavanones involves condensation of an appropriately protected hydroxyacetophenone with an appropriately protected 3-hydroxy-4-alkoxybenzaldehyde in the presence of base to give a chalcone which is then converted to the desired flavanone by treatment with strong acid.

This route may be shown as follows:

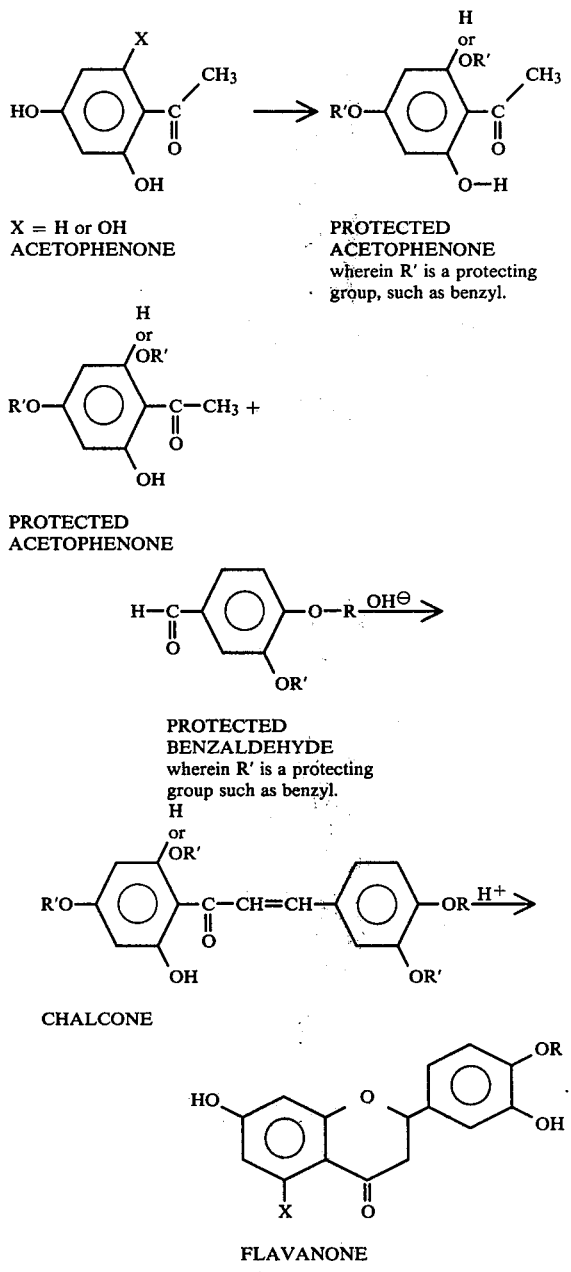

As will be now shown, these steps can be carried out with process conditions and reagents known to those skilled in the art. The protected hydroxyacetophenone derivatives, such as 2-hydroxy-4,6-dibenzyloxyacetophenone and 2-hydroxy-4-benzyloxyacetophenone, are prepared from the requisite commercially available hydroxyacetophenones by treatment with a reagent such as a benzyl halide, particularly benzyl bromide or iodide, or chloride (1.00–1.25 equivalent based upon the number of hydroxyl groups to be reacted) at 25°–80° C. in polar aprotic liquid phase media. Suitable media include N,N-dimethylformamide (DMF), dimethylsulfoxide, hexamethylphosphoramide, and the like. An acid acceptor, such as a metal bicarbonate, carbonate, or hydroxide, especially an alkali metal such as $K^+$ of a bicarbonate, carbonate or hydroxide, is also added to the reaction mixture in an amount of from 0.8 to 1.5 equivalents per mole of hydroxyl group being protected. Generally, long reaction times, such as at least 12 hours, are employed with these mild conditions. The most preferred method for preparing the protected hydroxyacetophenones involves the use of benzyl chloride (1.1 equivalent) and $K_2CO_3$ (1.0 equivalent) in DMF at 25°–40° C. Under these conditions the reactions are complete within 3–4 days, with product isolation being carried out by means of a standard aqueous workup.

The protected 4-alkoxy-3-hydroxybenzaldehydes, needed for condensation with the protected hydroxyacetophenones, are prepared by a two-step process from 3,4-dihydroxybenzaldehyde (protocatechualdehyde; commercially available). The first step, which is the preparation of the intermediate 4-alkoxy-3-hydroxybenzaldehydes, involves the treatment of the 3,4-dihydroxybenzaldehyde with 1.0–1.1 molar equivalents of a 1–3 carbon alkyl halide (especially iodide) in a polar aprotic solvent, such as DMF, at room temperature or slightly above (15°–40° C.). An acid acceptor, such as an alkali metal carbonate, bicarbonate or hydroxide and preferably $K_2CO_3$, in a molar amount about equal to the moles of alkyl halide is required for this reaction. When carried out under these mild conditions, the hydroxyl group at the 4-position, being somewhat more reactive than the hydroxyl group at the 3-position, is alkylated almost exclusively. Protection of the remaining hydroxyl is then effected preferably by benzylation such as at 25°–50° C. with either benzyl chloride or benzyl bromide in DMF or a similar solvent containing 1.0–1.2 molar equivalents of $K_2CO_3$. This completes the preparation of the 4-alkoxy-3-benzyloxy-benzaldehydes or their otherwise protected equivalents.

The aldol condensation of the protected hydroxyacetophenones with the 4-alkoxybenzaldehydes, to afford a chalcone, is best carried out with a slight molar excess (preferably 1.1 to 1.5 molar equivalents, basis acetophenone) of benzaldehyde in a lower alkanol (methanol, ethanol, isopropanol) at room temperature to 75° C. A large excess (10–20 molar equivalents) of a strong base, such as NaOH, KOH, NaOEt, or t-BuOK, is needed in order for this reaction to proceed at a reasonable rate. The preferred method for conducting this aldol condensation is to utilize about 1.25 molar equivalents of the benzaldehyde and about 15 molar equivalents of 60% aqueous KOH in absolute ethanol (1.0 ml/mmol of acetophenone) at 20°–30° C. Under these conditions, the condensation is complete within 72 hours. The chalcone products may be isolated, after neutralization of the reaction mixture, by either a standard aqueous workup or by evaporating the reaction mixture to dryness and then extracting the product from the salts. Purification is carried out by recrystallization, with ethanol being the preferred solvent.

The chalcones, when protected as preferred with benzyl groups, undergo debenzylation with concomitant cyclization to the flavanones upon treatment with excess very strong mineral acid. Aqueous HI or HBr (10–20 molar equivalents) in glacial acid (20–60 ml/mmol of chalcone) are preferred acids and are employed at mildly elevated temperatures (30°–100° C.) In general, these reactions proceed rather poorly with other mineral acids, such as HCl, $H_2SO_4$, or $HClO_4$. The product flavanones are isolated, as a mixture with the resulting benzyl halide coproduct, by a standard aqueous workup. Purification is best accomplished by chromatographic techniques, such as thick layer chromatography or column chromatography. All of these reactions may be advantageously carried out with stirring and under an inert gas atmosphere.

Use of the Dihydrochalone Products

The dihydrochalcone products of this invention are sweet. The sweetness is intense—300–500 times that of sucrose. The sweetness is pure—greater than 85% of the flavor is sweet. The timing of the sweetness is sucrose-like. The taste sensation arrives quickly and departs without substantial linger in an excellent mimic of sucrose.

The dihydrochalcone products of this invention are sweet. They may be used as nonsucrose sweeteners for edibles (i.e., comestibles) such as foods, medicaments and beverages. In this use they may be admixed such as by dissolving or dry mixing with the edible in an amount about 1/100–1/1000 that which would be appropriate for sucrose. Thus, amounts of from about 0.2 to 0.005% by weight (basis edibles) may be employed.

One difficulty should be noted in the usefulness of these materials. The compounds, especially in a high state of purity, are very prone to crystallize out of solution, especially out of cold, weakly acidic (pH 2–7) solely aqueous solutions.

One may, however, minimize the impact of this property in a number of ways. For example, one may use the salt forms, especially the mono and di-alkali and alkaline earth salts (especially potassium or sodium) and ammonium salts. Such forms offer improved solubility such as for dry table-top sweetener use. Another approach is to use the compounds with an organic cosolvent or solubilizer. Suitable materials are organic liquids such as glycerol and propylene glycol as well as aqueous solutions of materials such as sorbitol (70% aqueous solution) and erythritol aqueous solution. These organic solubilizers may be added advantageously in the range of from 0.1% by weight to 5% by weight (preferably 0.2% by weight to 3% by weight) basis total solution. Additionally, many consumable systems contain suspended or dissolved materials which beneficially interfere with crystallization and thus improve solubility. For example, brewed coffee contains solids and oils which enhance solubility. Yet another approach to minimizing the problem of marginal solubility, as it might appear in soft drink beverage systems, is to incorporate the sweetener into the highly acidic beverage concentrate (contains phosphoric acid) prior to diluting the concentrate rather than after dilution.

The present invention will be further shown by the following examples. These are intended to exemplify the invention and are not to be construed as limiting its scope.

EXAMPLES

Preparation of Precursors

I. Methyl 2-(N-carbobenzyloxy)amino-4-bromobutyrate

This compound is prepared by a modification of the procedure used by Nollet, Huting and Pandit to prepare tertiary butyl 2-(N-carbobenzyloxy)amino-4-bromobutyrate. (*Tetrahedron*, 25, 5971 (1969))

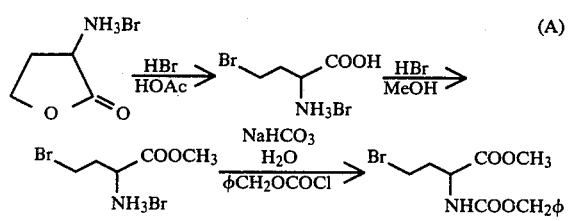
(A)

To 3.64 g (20.0 mmoles) of 2-aminobutyrolactone hydrobromide is added 182 ml of glacial acetic in a 500 ml three-necked flask equipped with a fritted glass gas bubbler, calcium chloride drying tube, and magnetic stirrer. Hydrogen bromide gas is then vigorously bubbled into the resultant suspension while stirring at ambient temperature. After three hours, all of the starting material has gone into solution and hydrogen bromide addition is discontinued. The reaction mixture is stirred at ambient temperature overnight and then is concentrated to dryness at reduced pressure yielding 5.2 g of crude 2-amino-4-bromobutyric acid hydrobromide as a white solid. This crude acid is dissolved in 25 mls absolute methanol after which hydrogen bromide gas is bubbled in for one minute. Monitoring reaction progress by NMR ($BrCH_2$—:$CH_3$—O-integration) indicates negligible reaction after stirring overnight at room temperature. After refluxing for 72 hours the reaction is judged to be complete. The reaction mixture is then concentrated to dryness at reduced pressure yielding crude methyl 2-amino-2-bromobutyrate hydrobromide as a colorless oil. To a solution of this crude ester in 25 ml water is added 3.70 g (44.0 mmoles) of sodium bicarbonate while stirring vigorously in an ice bath. Immediately, 3.8 mls (4.1 g; 24 mmoles) of benzylchloroformate is added dropwise over ca. two minutes. After ten minutes, the ice bath is removed, allowing the reaction mixture to warm to room temperature over 30 minutes. It is then poured into a separatory funnel and extracted with ether (3×25 ml), the combined portions of which are washed with saturated sodium bicarbonate (3×25 ml), dried over magnesium sulfate and concentrated, yielding 5.44 g of an oily white solid. Recrystallization from hexane-ether yields 1.96 of methyl-2-(N-carbobenzyloxy)-amino-4-bromo-butyrate (A) as white clusters having mp 87°–9°. This represents a 30% overall yield from 2-amino-butyrolactone hydrobromide. Tlc (Silica Gel F-254; $CHCl_3$) shows one spot having $R_f$=0.15.

IR: $\lambda_{Max}^{KBr}$ 2.95 (N—H), 3.32, 3.40, 5.83 (C=O), 6,59, 6.97, 7.46, 8.20, 9.02, 9.16, 10.90, 12.83, 13.36, 14.27μ.

NMR: δTMS/$CDCl_3$ 1.99–2.56 (2H multiplet, Br—C—$CH_2$—C—N—), 3.40 (2H triplet, J=7.2 Hz, Br—$CH_2$—, 3.76 (3H singlet, O—$CH_3$), 5.10 (2H singlet, Ar—O—$CH_2$, 5.30 (1H broad abs, N—H, 7.36 (5H singlet, aromatic H).

Anal. Calc. for $C_{13}H_{16}BrNO_4$:C, 47.28; H, 4.88. Found: C, 47.98; H, 4.95.

II. Flavanones by Condensing Aldehydes and Acetophenones

A. Preparation of Unprotected Aldehyde Reactants (1) A solution-suspension of 2.76 g (20.0 mmoles) of 3,4-dihydroxybenzaldehyde and 2.76 g (20.0 mmoles) of anhydrous potassium carbonate and 3.45 g (22.0 mmoles) of ethyl iodide is prepared in 15 ml of dry DMF and stirred under argon for 24 hours at room temperature. The reaction mixture is poured into 50 ml dilute HCl, saturated with sodium chloride and extracted thrice with diethyl ether. The ether extracts are washed with water, and brine, dried and concentrated to yield the ethoxyaldehyde as dark crystals.

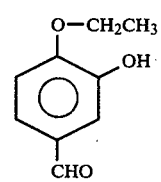

(2) The reaction is repeated using 3.74 g (22.0 mmoles) of n-propyl iodide in place of ethyl iodide to yield the propoxyaldehyde

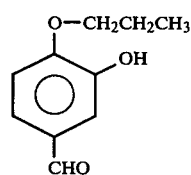

(3) The reaction could be repeated using 3.12 g (22.0 mmoles) of methyl iodide in place of ethyl iodide to yield the methoxyaldehyde

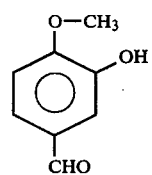

Alternatively, this material, isovanillin, is readily available, commercially.

(4) The reaction is repeated using 4.36 g (22.0 mmoles) of n-butyl iodide in place of ethyl iodide to yield the butoxyaldehyde

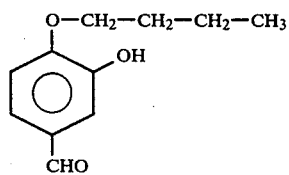

B. Preparation of 4-Alkoxy-3-benzyloxybenzaldehyde

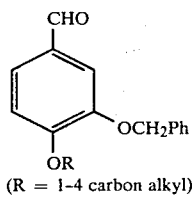

(R = 1-4 carbon alkyl)

4-Alkoxy-3-hydroxybenzaldehyde (1.0 equiv.), benzyl chloride (1.2 equiv.) and $K_2CO_3$ (1.2 equiv.) are stirred in anhydrous DMF at 35° C. for 72 hours. The reaction mixture is poured into dilute HCl, extracted thrice with ether and the combined extracts washed thoroughly with $H_2O$, dilute aqueous KOH (until the ether solution is free of unreacted hydroxybenzaldehyde as determined by TLC), $H_2O$ again, and finally brine. Evaporation affords crude 4-alkoxy-3-benzyloxybenzaldehyde which is generally suitable for use, as is, in the condensation reaction. Additonal purification may be achieved by silica gel column chromatography.

C. Preparation of Protected Acetophenones (1) Preparation of 2-Hydroxy-4,6-dibenzyloxyacetophenone

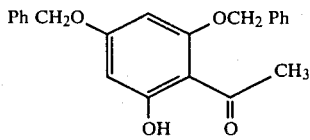

2,4,6-Trihydroxyacetophenone (16.8 g, 0.10 mol, Aldrich Chemical Company) and benzyl chloride (27.8 g, 200 mol) are dissolved in 200 ml of dry DMF and the solution is thoroughly purged with argon. The mixture is treated with 27.6 g (0.20 mol) of $K_2CO_3$ and stirred at 35° C. for 84 hours. The reaction is poured into ether (1200 ml) and resulting mixture washed with $H_2O$ (6×500 ml), 5% aqueous KOH solution (3×500 ml), $H_2O$ (1×500 ml), and saturated NaCL solution (1×250 ml). After drying over $MgSO_4$, the ethereal solution is evaporated to afford 27.4 g of crude product as an off-white granular solid. Trituration of the crude product with ether (100 ml), followed by filtration and drying in vacuo provides 13.5 g (38.8%) of 2-hydroxy-4,6-dibenzyloxyacetophenone as a white solid, mp 101°-102° C., i.e.,

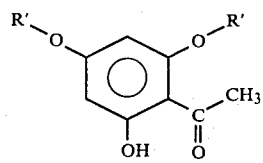

wherein R' is benzyl.

The product is homogeneous by silica gel TLC ($CHCl_3$ elution) and the assigned structure is verified by both NMR and elemental analysis.

(2) Preparation of 2-hydroxy-4-benzyloxyacetophenone

The reaction of (1) above is repeated using 1.1 molar equivalents of benzyl chloride, 1.0 molar equivalent of $K_2CO_3$, and substituting for the above acetophenone 2,4-dihydroxyacetophenone

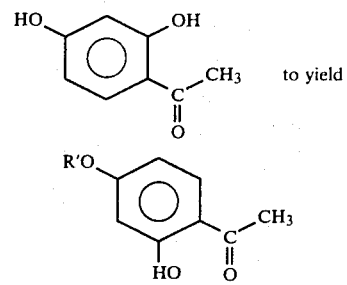

D. Preparation of 2-Hydroxy-3', 4,6-tribenzyloxy-4'-alkoxychalcone

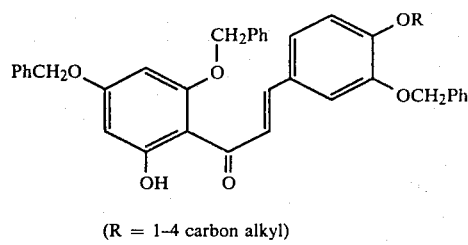

(R = 1-4 carbon alkyl)

Twelve mls of warm 60% aqueous KOH is added rapidly to a solution of 2.79 g (8.00 mmoles) 2-hydroxy-4,6-dibenzyloxyacetophenone and 1.00 equivalent (8.00 mmoles) 3-benzyloxy-4-alkoxybenzaldehyde in a mixture of 16 mls absolute ethanol and 16 mls tetrahydrofurane while stirring vigorously under argon. After 16 hours, the reaction mixture is poured into an excess of ice-cold HCl and the precipitated yellow chalcone isolated by filtration. After washing with $H_2O$ and air drying, the chalcone is recrystallized from ethanol-ethylacetate to yield the pure chalcone as tiny yellow needles (65-90%). Product identity and purity are determined by TLC [Hexane-Ethyl Acetate (1:1)], proton nmr and elemental analysis.

E. Preparation of 3', 5,7-Trihydroxy-4'-alkoxyflavanone

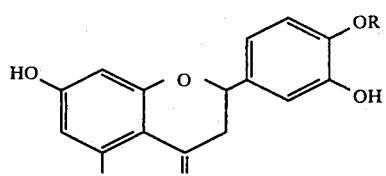

(R = 1-4 carbon alkyl)

A. 1.0 mmol sample of 2-hydroxy-3'4,6-tribenzyloxy-4'-alkoxychalcone is dissolved in 40 ml of glacial acetic acid at 60° C. and treated with 2 ml of 48% aqueous HBr. The yellow solution becomes deep reddish-orange upon addition of the acid. After stirring 24 hours at this temperature, the reaction mixture is poured into $H_2O$ (200 ml) and the resulting aqueous mixture extracted with an equal volume of ethyl acetate. The organic extract is washed with $H_2O$ (2×100 ml), 5% aqueous $NaHCO_3$ solution (2×100 ml), $H_2O$ (1×100 ml), saturated aqueous NaCl solution (1×50 ml), and dried over $MgSO_4$. Evaporation affords the crude flavanone admixed with three equivalents of benzyl bromide.

Silica gel column chromatography (elution with ethyl acetate-hexane, (1:1) affords flavanone (30–60%) as an off-white crystalline solid, which may be further purified by recrystallization. Product identity and homogeneity are determined by silica gel TLC (ethyl acetate-hexane, 1:1), proton NMR, and elemental analysis.

F. The coupling, exemplified by Parts D. and E., is repeated six more times varying the aldehyde among the four materials of Part A. of this preparation and the two acetophenones of Part B. so, with the materials of D. and E., as to yield the eight possible flavanones of General Formula II which can result when X is H or OH and R is $CH_3$, $C_2H_5$, $C_3H_7$ or $C_4H_9$.

EXAMPLE I

Preparation of Dihydrochalcone Wherein X is OH and R is $CH_3$

A.
3,5-Dihydroxy-4'-methoxy-7-(3-(N-carbobenzyloxy)amino-3-carbomethoxy-propoxy)-flavanone

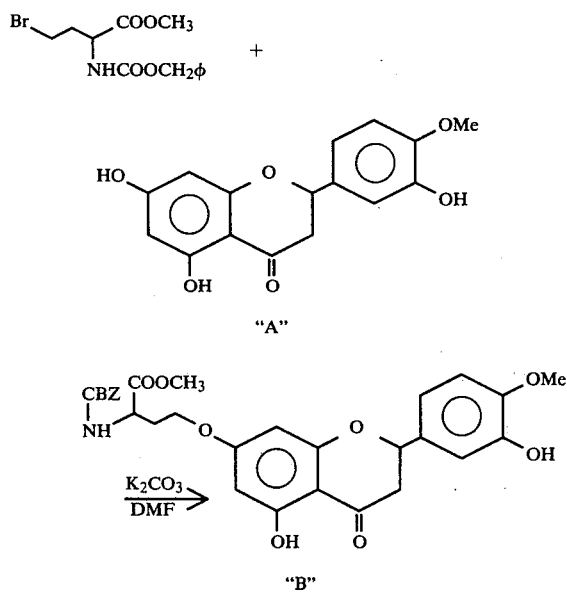

Seven mls of dry dimethylformamide are added to a mixture of 302 mg (1.00 mmole) hesperetin, 152 mg (1.10 mmoles) anhydrous potassium carbonate, and 330 mg (1.00 mmole) of methyl 2-(N-carbobenzyloxy)-amino-4-bromo-butyrate, made as above. The resulting mixture is stirred vigorously under an argon atmosphere at 35° overnight after which it is diluted with 40 mls water, acidified to pH 5 with 1N HCl and extracted with ethyl acetate (3×25 ml), the combined portions of which are washed with water (2×20 ml), brine (1×20 ml), dried over magnesium sulfate and concentrated yielding 585 mg of an off-white foam. Purification by preparative Tlc (Silica Gel PF-254; $CH_2Cl_2CH_3OH$ [98:2]) yields 368 mg (67%) of the pure alkylation product "B" as a colorless oil. Tlc (Silica Gel F-254; $CH_2Cl_2$—$CH_3OH$ [98:2]) showed one spot having $R_f = 0.22$.

IR: $\lambda_{max}^{film}$ 2.96 (O—H), 3.24, 3.36, 3.44, 5.81 (ester, carbamate C=O), 6.09 (ketone C=O), 6.35, 6.54 6.62, 6.85, 6.96, 7.30, 7.48, 7.73, 7.89, 8.06, 8.38, 8.61, 8.85, 9.19, 9.40, 9.59, 9.75, 11.52, 12.43, 13.13, 13.48, 14.35μ, NMR: $\delta_{CDCl_3}^{TMS}$ 2.00–2.53 (2H multiplet, —O—C—$CH_2$—N—), 3.72 (3H singlet, —$COOCH_3$), 3.87 (3H singlet, Ar'—O—$CH_3$), 4.00 (2H triplet, J-7.4 Hz, —O—$CH_2$—C—C—N—), 4.36–4.70 (1H multiplet, —CH—N—), 5.10 (2H singlet, $PhCH_2O$—), 5.10–5.39 (1H multiplet, Ar—O—CH—Ar'), 6.00 (2H singlet, Ar aromatic H), 6.76–7.07 (3H multiplet, Ar' aromatic H), 7.37 (5H singlet, benzyl aromatic H), 11.98 (1H singlet, Ar—O—H).

B.
2,3'6-Trihydroxy-4-(3-amino-3-carboxy-propoxy)-4'-methoxy-dihydrochalcone

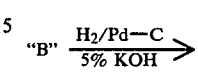

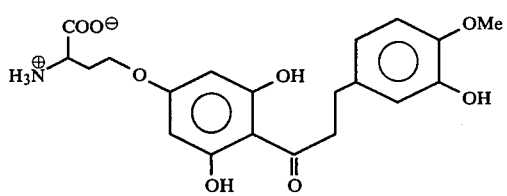

To a solution of 368 mg (0.67 mmole) of flavanone B in 35 mls of 5% potassium hydroxide is added 210 mg of 5% Pd-C while under an argon atmosphere. The resultant reaction mixture is shaken on a Parr hydrogenator at 30 lb hydrogen pressure for 15 hours after which it is filtered through celite yielding a light green solution. Adjustment of the pH to 6 with 10% HCl results in formation of a large amount of off-white precipitate. Filtration yields 151 mg (56%) of the pure amino acid as a white solid having mp 182°–4° (dec). Tlc (cellulose F-254; i-BuOH-HOAc-$H_2O$ [2:1:1]) shows one spot having $R_f = 0.73$. HPLC on a Waters Associates instrument (30 cm C-18 on μ-Bondapak column eluting with 10–100% methanol in 0.03 M $NaH_2PO_4$ buffer (pH=4.8) gradient and employing a Schoeffels UV detector [286 nm]) shows one peak having RT=12.2 minutes.

IR: $\lambda_{Max}^{KBr}$ 2.90 (O—H, N—H), 6.36 (C=O), 6.42 (C=O), 6.62, 7.00, 8.37, 8.69, 9.22, 11.27, 12.3μ.

UV: $\lambda_{Max}^{MeOH}$ 226 ($\epsilon = 1.47 \times 10^4$), 284($\epsilon = 1.45 \times 10^4$)nm.

NMR: $\delta_{CD_3OD}^{TMS}$ 2.04–2.55 (2H multiplet, O—C—$CH_2$—C—N), 2.51–2.98 (4H multiplet, Ar—$COCH_2CH_2$—Ar'), 3.82 (3H singlet, O—$CH_3$), 3.90–4.36 (3H multiplet, O—$CH_2$, C—CH—N), 5.98 (2H singlet, Ar aromatic H), 6.60–6.93 (3H multiplet, Ar' aromatic H).

ANAL. Calc. for $C_{20}H_{23}NO_8$: C, 59.25, H, 5.72. Found: C, 56.12; H, 5.89.

As already noted, the dihydrochalcone may exist as the zwitterion prepared in Example I or as the protonated acid or as several deprotonated base forms. Example II shows the production of the deprotonated base forms, while Example III shows production of the protonated acid form.

EXAMPLE II

A. Preparation of Monopotassium salt of 2,3', 6-trihydroxy-4-(3-amino-3-carboxypropoxy)-4'-methoxy dihydrochalcone.

Twenty-five mls of dioxane (distilled from $LiAlH_4$) is added to 405 mg (1.00 mmole) of the dihydrochalcone of Example I. After addition of 5 mls of distilled water, a homogeneous solution is obtained to which 10.00 mls of 0.10 N aqueous KOH (1.00 mmole) is added. The resultant light yellow solution is then lyophilized to yield the monopotassium salt as a solid.

B. The preparation of Part A. is repeated with one change, 2.00 mmoles of KOH are added so as to yield the dipotassium salt.

C. The preparations of Parts A. and B. are repeated with one further change, NaOH is substituted for KOH.

D. A solution of 1.0 equivalent ammonia in methanol is added to a solution of 1.00 eq of the dihydrochalcone of Example I in methanol. The ammonium salt thus formed is then precipitated by addition of ether, isolated by filtration, washed with several portions of ether and dried in a dessicator over KOH pellets.

EXAMPLE III

Preparation of Conjugate Acid Salts

A. Twenty-five mls of dioxane (distilled from LiAlH$_4$), are added to 405 mg (1.00 mmole) of the amino acid of Example I. After addition of 5 mls of distilled water, a homogeneous solution is obtained to which 10.00 mls of 0.10 M H$_2$SO$_4$ (1.00 mmole) are added. The resulting solution is lyophilized to yield 504 mg of a hygroscopic white solid.

B. The preparation of step A, is repeated substituting an equimolar amount of HClO$_4$ for H$_2$SO$_4$.

EXAMPLE IV

Preparation of dihydrochalcone wherein X is H, R is CH$_3$

The preparation of Example I is repeated with one modification. In place of 1.1 equivalents of hesperetin, an equimolar amount of the flavanone of General Formula IV, wherein X is H and R is CH$_3$ and prepared at C(2) above, is employed. This gives rise to the dihydrochalcone of Formula I wherein X is H and R is CH$_3$.

EXAMPLE V

Preparation of dihydochalcones wherein X is H and OH and R is C$_2$H$_5$, C$_3$H$_7$ and C$_4$H$_9$ The preparation of Example I is repeated four more times. Each time, a new flavanone prepared at C. above is employed. This results in the formation of the dihydrochalcones in accord with Formula I with the following substituents:

| R | X |
| --- | --- |
| C$_2$H$_5$ | OH |
| C$_2$H$_5$ | H |
| C$_3$H$_7$ | OH |
| C$_3$H$_7$ | H |
| C$_4$H$_9$ | OH |
| C$_4$H$_9$ | H |

EXAMPLE VI

Preparation of Salts

The salt preparations of Examples II and III are repeated using as the dihydrochalcones those materials made in Examples IV and V.

EXAMPLE VII

Use of the Dihydrochalcones and Their Salts as Sweeteners

The compounds of Examples I through IV are employed as sweeteners. In this application they are some 350–450 times as intense (on a weight basis) as sucrose.

In typical applications they may be used as follows.

A 250 mg portion of the material of Example I is placed in a vessel. Ten mls of propylene glycol are then added. The mixture is warmed (45°–50° C.) with gentle stirring. The dihydrochalcone dissolves.

Two ml aliquots are withdrawn and diluted with distilled water, coffee, an unsweetened carbonated cola beverage and an unsweetened cough syrup. In each case a pleasant sucrose-like sweet taste is imparted to the diluent substrate.

A similar experiment is conducted using glycerol as solubilizing agent with essentially the same results.

The experiment can also be repeated using the dihydrochalcones of Examples IV and V and the salts of Examples II, III and VI.

What is claimed is:

1. The dihydrochalcone represented by the formula

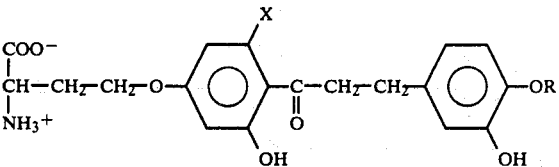

wherein X is selected from between hydrogen and hydroxy and R is an alkyl of from one to four carbon atoms.

2. The dihydrochalcone of claim 1 wherein X is hydroxy and R is selected from among methyl, ethyl, n-propyl and n-butyl.

3. The dihydrochalcone represented by the formula

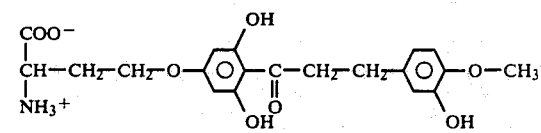

4. The dihydrochalcone represented by the formula

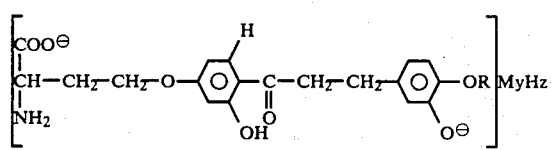

wherein M is a physiologically acceptable cation, R is an alkyl of from 1 to 4 carbons, and y and z are positive numbers, the sum of which is 2.

5. The dihydrochalcone of claim 4 wherein R is CH$_3$ and M is selected from among the cations of potassium, sodium, calcium and magnesium.

6. The dihydrochalcone represented by the formula

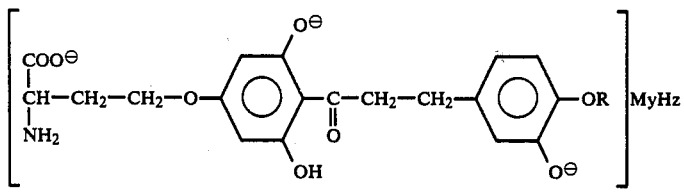

wherein M is a physiologically acceptable cation, R is an alkyl of from 1 to 4 carbons, and y and z are positive numbers, the sum of which is 3.

7. The dihydrochalcone of claim 6 wherein R is $CH_3$ and M is selected from among the cations of potassium, sodium, calcium and magnesium.

8. The dihydrochalcone of claim 7 wherein y is about 1 and z is about 2.

9. The dihydrochalcone of claim 8 wherein M is potassium cation.

10. The dihydrochalcone of claim 7 wherein y is about 2 and z is about 1.

11. The dihydrochalcone of claim 10 wherein M is potassium cation.

12. The dihydrochalcone representated by the formula

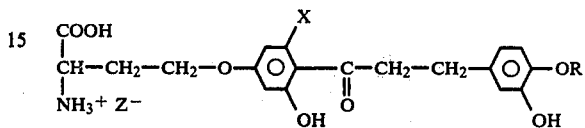

wherein $Z^-$ is a physiologically acceptable conjugate base of a strong acid, X is selected from between hydrogen and hydroxyl, and R is an alkyl of from one to four carbon atoms.

13. The dihydrochalcone of claim 12 wherein R is $CH_3$ and X is OH.

* * * * *